(12) United States Patent
Palumbo et al.

(10) Patent No.: US 6,190,369 B1
(45) Date of Patent: Feb. 20, 2001

(54) DISPOSABLE ABSORBENT ARTICLE HAVING IMPROVED IN-USE STORAGE CAPACITY FOR LOW AND MEDIUM LOW VISCOSITY FECES

(75) Inventors: Gianfranco Palumbo, Bad Homburg; Vincenzo D'Acchioli, Kelkheim, both of (DE)

(73) Assignee: The Procter & Gamble Company, Cincinnati, OH (US)

( * ) Notice: Under 35 U.S.C. 154(b), the term of this patent shall be extended for 0 days.

(21) Appl. No.: 09/230,430

(22) PCT Filed: Jul. 16, 1997

(86) PCT No.: PCT/US97/12506

§ 371 Date: Jan. 25, 1999

§ 102(e) Date: Jan. 25, 1999

(87) PCT Pub. No.: WO98/03138

PCT Pub. Date: Jan. 29, 1998

(30) Foreign Application Priority Data

Jul. 24, 1996 (EP) .................................................. 96111895

(51) Int. Cl.[7] ................................ A61F 5/44; A61F 13/15
(52) U.S. Cl. .................... 604/385.01; 604/348; 604/378; 604/385.19
(58) Field of Search ..................................... 604/348, 378, 604/385.1

(56) References Cited

FOREIGN PATENT DOCUMENTS 62-276002   11/1987   (JP) ............................... A41B/13/02

*Primary Examiner*—John G. Weiss
*Assistant Examiner*—Paul Shanoski
(74) *Attorney, Agent, or Firm*—David M. Weirich; Ken K. Patel; Steven W. Miller

(57) ABSTRACT

A disposable absorbent article, such as a diaper, comprising a medium viscosity feces storage material having an improved ability to store in particular medium low viscosity feces.

9 Claims, 3 Drawing Sheets

DISPOSABLE ABSORBENT ARTICLE HAVING IMPROVED IN-USE STORAGE CAPACITY FOR LOW AND MEDIUM LOW VISCOSITY FECES

FIELD OF THE INVENTION

This invention relates to disposable absorbent articles, such as diapers and adult incontinence products, and more particularly to disposable absorbent articles which have the capacity to retain low and medium-low viscosity feces and thus keep these away from the skin of the wearer, in order to reduce leakage and make it easier to clean the wearer when the soiled disposable absorbent article is removed.

BACKGROUND OF THE INVENTION

Disposable absorbent articles such as diapers and adult incontinence products are well known in the art. Such disposable absorbent articles collect and retain urine and feces deposited thereon by the wearer. While a great deal of effort has been and still is spent against improving the handling of urine, relatively little has been done to improve the handling of feces, in particular when dealing with low or medium viscosity feces.

Feces can be discharged by the wearer over a wide range of amounts, number of occurrences, consistency, depending on the age (newborn to adults) or condition of the wearer (nutrition, sicknesses, etc.). It is said, that daily loadings can average between 100 gram to over 1000 g under pathologic conditions, with individual daily loadings being as low a 40 grams. The loading frequency is generally higher with small babies (newborn up to five occurrences per day), and decreasing with age to about once per day for adults. Composition is also very variable, but within the scope of the present invention the amount of water is of particular interest, which can range from about 70% to about 90% of total discharge. Correspondingly, the consistency of such discharges (often referred to a as "bowel movements" or abbreviated "BM") can range from "firm" over "pasty" to "runny". Within the scope of the present invention, this consistency can best be correlated with the technical measure of viscosity.

Obviously, the handling of such materials requires very different structures as compared to the structures for "storage" or absorbency of fluids like urine. For the latter, a much smaller pore sizes is required (which can be even as small as to molecular size, such as provided by "superabsorbent materials", though there in addition to other effects). Storage of feces however, requires sufficiently open/large pores for being able to receive the feces, which—in comparison to urine—have a much higher viscosity. This requirement applies both to the topsheet (facing) materials of an absorbent article, and also to materials which are supposed to store respective materials.

Attempts to improve the handling of feces include providing a first topsheet which conforms closely to the wearer and has an aperture. The aperture is hopefully registered with the anal opening, so that feces passes there through into a void space. The first topsheet may comprise various elastic panels in order to closely conform to the skin of the wearer, and/or may have linear elastic strands. Improvements have been made in this area of the prior art, such as optimizing the material properties of the first topsheet. Such optimization makes the first topsheet more comfortable to the wearer and allows a single disposable absorbent article to fit a larger range of sizes of wearers. Examples for such approaches are given in EP-A-0 359 410; EP-A-0 386 816; EP-A-0 644 747.

Further improvements to this type of the prior art disposable absorbent articles also include the addition of spacers. Spacers may be interposed between the first topsheet and the core, in order to ensure a void space is present to receive the feces. Examples for these approaches are given in U.S. Pat. No. 4,778,459; FR-2 495 899; WO 90/14063; WO 93/12748.

Yet other attempts have been made for such types of the prior art articles by providing barriers which limit the movement of feces to particular portions of the disposable absorbent article. The barriers limit the contact of the feces to a lesser portion of the skin of the wearer, than a comparable disposable absorbent article which has no barriers. Such approaches are disclosed in U.S. Pat. No. 5,514,121; EP-A-0 486 006.

However, none of these attempts to handle feces solve the specific problems which occur when feces of a softer consistency is present, such as being prevalent for younger children, particularly those who are breast fed. Such lower viscosity feces are referred to by mothers as "runny bowel movement (or BM)" corresponding to low-viscosity feces, or "pasty BM" for feces of a higher consistency, which however still has a much lower viscosity than "firm BM". Such lower viscosity feces easily migrate within the disposable absorbent article under the influences of gravity and motion or pressure by the wearer.

The migration of the feces often results in movement of it on the surface of the absorbent article towards the perimeter of the disposable absorbent article, increasing the likelihood of leakage. The migration of the feces also smears it against the skin of the wearer, making cleanup more difficult. In order to clean the wearer, the caretaker must wipe the entire area of the skin which has encountered the feces and typically has to deal with a relatively large soiled area.

One serious attempt in the art to handle low-viscosity feces is found in U.S. Pat. No. 5,342,338. This application describes a disposable absorbent article having a first topsheet with a high trans-topsheet penetration overlaying a secondary topsheet having a lesser trans-topsheet penetration.

PCT US 94/08958 discloses further a disposable absorbent article which reduces leakage of low-viscosity feces from the disposable absorbent article and aims at minimizing the amount of low-viscosity feces remaining on the skin of the wearer once the disposable absorbent article is removed by combining a topsheet with high trans-topsheet penetration and a fecal storage material.

However, the prior art referred to herein before is relying on in-use movements to create storage space, such as by allowing the topsheet to detach from the underlying fluid storage structure possibly enhanced by elastic features. Hence it is an object of the current invention, to provide such storage space from the beginning of the use period and to further maintain such storage space during use.

Hence it is an object of the invention to provide structures with improved feces handling properties especially for medium viscosity feces, as expressed by improved feces storage capacity.

It is a further object of the invention to allow selection of the appropriate materials for such improved structures by assessing the medium viscosity feces storage capacity, related to either the amount of material used or the area of the material.

BRIEF SUMMARY OF THE INVENTION

A disposable absorbent article, such as a diaper, comprising a medium viscosity feces storage material having an improved ability to store in particular medium low viscosity feces. Such storage materials are characterized in having a feces storage capacity of at least 20 g/g, preferably of more than 35 g/g, when tested according to the described test for medium viscosity fecal storage capacity.

BRIEF DESCRIPTION OF THE DRAWINGS

While the Specification concludes with claims pointing out and distinctly claiming the present invention, it is believed the same will be better understood by the following drawings taken in conjunction with the accompanying Specification wherein like components are given the same reference number and:

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A preferred embodiment of an absorbent article of the present invention is the disposable absorbent article, diaper 20, shown in FIG. 1. As used herein, the term "diaper" refers to an absorbent article generally worn by infants and adult incontinent persons and is worn about the lower torso of the wearer.

Figure 1A:
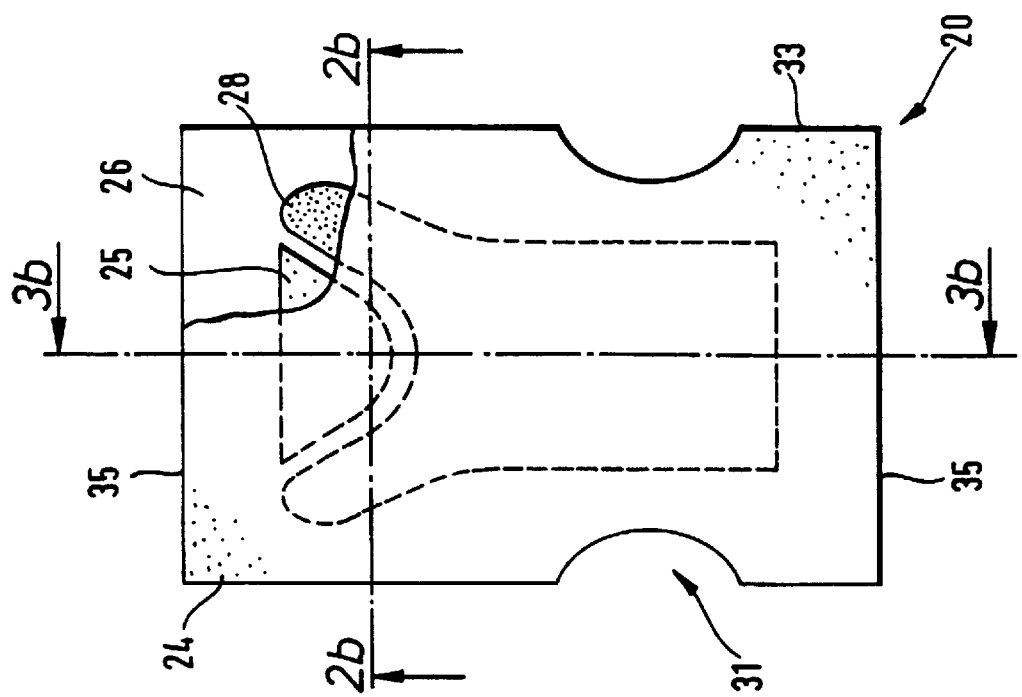
FIGS. 1a and b are a top plan view, shown partially in cutaway, of disposable absorbent article according to the present invention with two different arrangements of the absorbent core and the storage material.
Figure 1B:
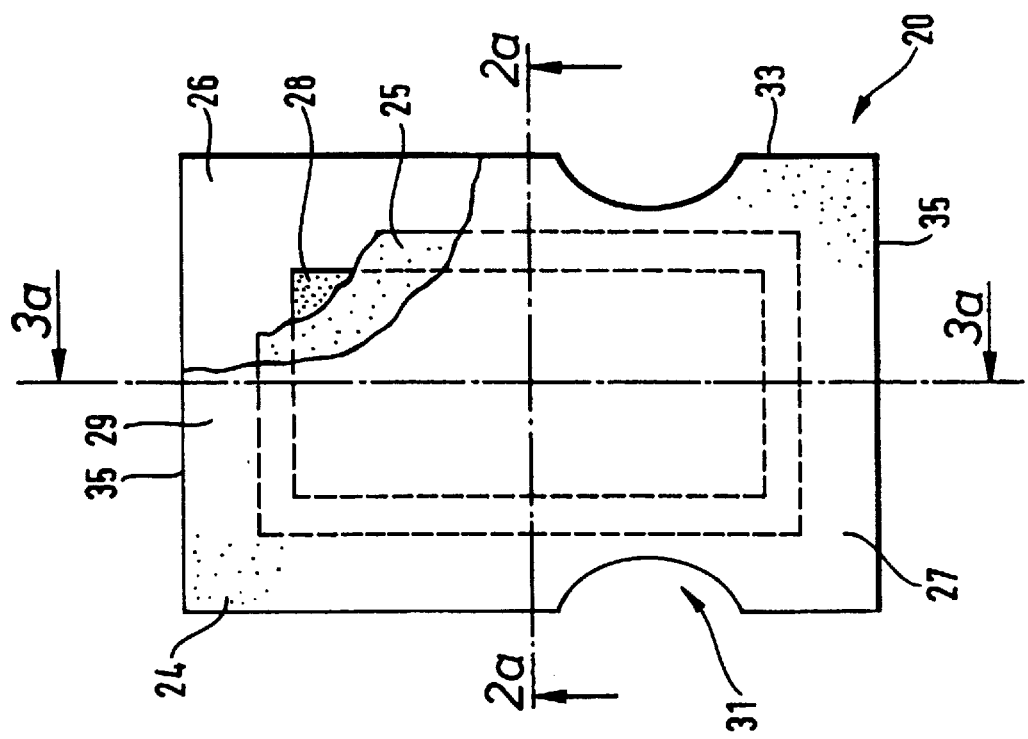

FIG. 1 is a plan view of the diaper 20 of the present invention in its flat-out, uncontracted state (i.e., with elastic induced contraction pulled out) with portions of the structure being cut-away to more clearly show the construction of the diaper 20 and with the portion of the diaper 20 which faces or contacts the wearer, the inner surface, oriented towards the viewer. As shown in FIG. 1, the diaper 20 preferably comprises a liquid pervious first topsheet 24; a liquid impervious backsheet 26 joined with the first topsheet 24; a liquid pervious feces storage material 25 intermediate the first topsheet 24 and the backsheet 26; and optionally an absorbent core 28 intermediate the feces storage material 25 and the backsheet 26. This absorbent core 28 is generally intended and designed to absorb urine and can, of course, also pick up certain amounts of the feces, such as aqueous portions. Thus, the feces storage material 25 can be a separate component than absorbent core 28, or integral with absorbent core 28, or a combination thereof. The diaper 20 may further comprise elasticized side panels (not shown); elasticized leg cuffs (not shown); an elastic waist feature (not shown); and a fastening system with tape tabs—(not shown)—.

The diaper 20 is shown in FIG. 1 to have a first waist region 27 juxtaposed with the front of the wearer while the diaper 20 is being worn, a second waist region 29 opposed to the first waist region 27 and juxtaposed with the back of the wearer while the diaper 20 is being worn, a crotch region 31 positioned between the first waist region 27 and the second waist region 29, and a periphery which is defined by the outer edges of the diaper 20 in which the longitudinal edges are designated 33 and the end edges are designated 35. The inner surface of the diaper 20 comprises that portion of the diaper 20 which is adjacent to the wearer's body during use (i.e., the inner surface generally is formed by at least a portion of the first topsheet 24 and other components joined to the first topsheet 24). The outer surface comprises that portion of the diaper 20 which is positioned away from the wearers body (i.e., the outer surface generally is formed by at least a portion of the backsheet 26 and other components joined to the backsheet 26) during use.

Figure 2B:
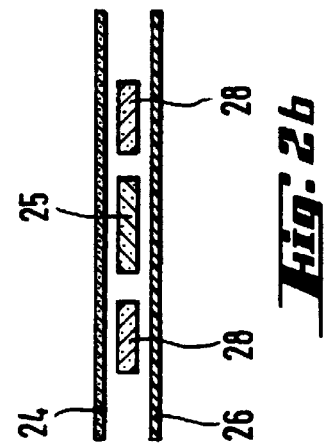
FIGS. 2a and b are a vertical sectional view taken along the cross-directional lines 2—2 of FIGS. 1a and b, showing the relationship of the first topsheet, feces storage material and absorbent core.
Figure 2A:
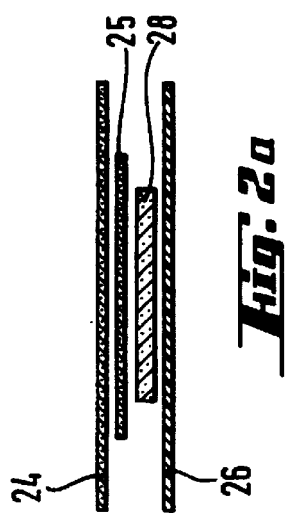

FIG. 2 shows an embodiment of the diaper 20 in which the first topsheet 24 and the backsheet 26 have length and width dimensions generally larger than those of the absorbent core 28. The first topsheet 24 and the backsheet 26 extend beyond the edges of the absorbent core 28 to thereby form the periphery of the diaper 20. Alternatively, the feces storage material 25 may, but need not, extend beyond the edges of the absorbent core 28 and be joined to the backsheet 26 to form the periphery of the diaper 20 and the first topsheet 24 smaller than or coextensive of the core 28. While the first topsheet 24, the feces storage material 25, the backsheet 26, and the core 28 may be assembled in a variety of well known configurations, preferred diaper configurations are described generally in U.S. Pat. No. 3,860,003 entitled "Contractable Side Portions for Disposable Diaper" which issued to Kenneth B. Buell on Jan. 14, 1975; and U.S. Pat. No. 5,151,092, "Absorbent Article With Dynamic Elastic Waist Feature Having A Predisposed Resilient Flexural Hinge", issued to Kenneth B. Buell et al. Sep. 29, 1992.

The absorbent core 28 may be any absorbent means which is generally compressible, conformable, non-irritating to the wearer's skin, and capable of absorbing and retaining liquids such as urine. As shown in FIG. 1, the absorbent core 28 has a garment surface, a body surface, side edges, and waist edges. The absorbent core 28 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials.

The configuration and construction of the absorbent core 28 may also be varied (e.g., the absorbent core 28 may have varying caliper zones, a hydrophilic gradient, a superabsorbent gradient, or lower average density and lower average basis weight acquisition zones; or may comprise one or more layers or structures). The total absorbent capacity of the absorbent core 28 should, however, be compatible with the design loading and the intended use of the diaper 20.

Further, the size and absorbent capacity of the absorbent core 28 may be varied to accommodate wearers ranging from infants through adults.

Exemplary absorbent structures for use as the absorbent core 28 are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989.

The backsheet 26 is positioned adjacent the garment surface of the absorbent core 28 and is preferably joined thereto by attachment means (not shown) such as those well known in the art. As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element.

For example, the backsheet 26 may be secured to the absorbent core 28 by a uniform continuous layer of adhesive, a patterned layer of adhesive, or an array of separate lines, spirals, or spots of adhesive. Adhesives which have been found to be satisfactory are manufactured by H.B. Fuller Company of St. Paul, Minn. and marketed as HL-1258. The attachment means will preferably comprise an open pattern network of filaments of adhesive as is disclosed in U.S. Pat. No. 4,573,986 entitled "Disposable Waste-Containment Garment", which issued to Minetola et al. on Mar. 4, 1986, more preferably several lines of adhesive filaments swirled into a spiral pattern such as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Alternatively, the attachment means may comprise heat bonds, pressure bonds, ultrasonic bonds, dynamic mechanical bonds, or any other suitable attachment means or combinations of these attachment means as are known in the art.

The backsheet 26 is impervious to fluids like urine or feces, and is preferably manufactured from a thin plastic film, although other flexible liquid impervious materials may also be used. As used herein, the term "flexible" refers to materials which are compliant and will readily conform to the general shape and contours of the human body.

The backsheet 26 prevents the exudates absorbed and contained in the absorbent core 28 from wetting articles which contact the diaper 20 such as bedsheets and undergarments. The backsheet 26 may thus comprise a woven or nonwoven material, polymeric films such as thermoplastic films of polyethylene or polypropylene, or composite materials such as a film-coated nonwoven material. Preferably, the backsheet 26 is a thermoplastic film having a thickness of about 0.012 mm (0.5 mil) to about 0.051 mm (2.0 mils). Particularly preferred materials for the backsheet 26 include RR8220 blown films and RR5475 cast films as manufactured by Tredegar Industries, Inc. of Terre Haute, Ind. The backsheet 26 is preferably embossed and/or matte finished to provide a more clothlike appearance. Further, the backsheet 26 may permit vapors to escape from the absorbent core 28 (i.e., be breathable) while still preventing exudates from passing through the backsheet 26.

The diaper 20 may further comprise elasticized leg cuffs (not shown) which provide improved containment of liquids and other body exudates. Each elasticized leg cuff may comprise several different embodiments for reducing the leakage of body exudates in the leg regions. (The leg cuff can be and is sometimes also referred to as leg bands, side flaps, barrier cuffs, or elastic cuffs.) U.S. Pat. No. 3,860,003 describes a disposable diaper 20 which provides a contractible leg opening having a side flap and one or more elastic members to provide an elasticized leg cuff (gasketing cuff). Commonly assigned U.S. Pat. No. 4,909,803 entitled "Disposable Absorbent Article Having Elasticised Flaps" issued to Aziz et al. on Mar. 20, 1990, describes a disposable diaper 20 having "stand-up" elasticized flaps (barrier cuffs) to improve the containment of the leg regions. Commonly assigned U.S. Pat. No. 4,695,278 entitled "Absorbent Article Having Dual Cuffs" issued to Lawson on Sep. 22, 1987, describes a disposable diaper 20 having dual cuffs including a gasketing cuff and a barrier cuff.

The diaper 20 preferably further comprises an elastic waist feature (not shown) that provides improved fit and containment. The elastic waist feature is that portion or zone of the diaper 20 which is intended to elastically expand and contract to dynamically fit the wearer's waist. The elastic waist feature at least extends longitudinally outwardly from at least one of the waist edges of the absorbent core 28 and generally forms at least a portion of the end edge of the diaper 20. Disposable diapers are generally constructed so as to have two elastic waist features, one positioned in the first waist region 27 and one positioned in the second waist region 29, although diapers can be constructed with a single elastic waist feature. Further, while the elastic waist feature or any of its constituent elements can comprise a separate element affixed to the diaper 20, the elastic waist feature is preferably constructed as an extension of other elements of the diaper 20 such as the backsheet 26 or the first topsheet 24, preferably both the backsheet 26 and the first topsheet 24. The elasticized waistband 34 may be constructed in a number of different configurations including those described in U.S. Pat. No. 4,515,595 issued to Kievit et al. on May 7, 1985 and the above referenced U.S. patent application Ser. No. 07/715,152.

The diaper 20 also comprises a fastening system 36 which forms a side closure which maintains the first waist region 27 and the second waist region 29 in an overlapping configuration such that lateral tensions are maintained around the circumference of the diaper 20 to maintain the diaper 20 on the wearer. Exemplary fastening systems are disclosed in U.S. Pat. No. 4,846,815 entitled "Disposable Diaper Having An Improved Fastening Device" issued to Scripps on Jul. 11, 1989; U.S. Pat. No. 4,894,060 entitled "Disposable Diaper With Improved Hook Fastener Portion" issued to Nestegard on Jan. 16, 1990; commonly assigned U.S. Pat. No. 4,946,527 entitled "Pressure-Sensitive Adhesive Fastener And Method of Making Same" issued to Battrell on Aug. 7, 1990; commonly assigned U.S. Pat. No. 3,848,594 entitled "Tape Fastening System for Disposable Diaper" issued to Buell on Nov. 19, 1974; commonly assigned B1 U.S. Pat. No. 4,662,875 entitled "Absorbent Article" issued to Hirotsu et al. on May 5, 1987; and the herein before referenced U.S. patent application Ser. No. 07/715,152.

The diaper 20 is preferably applied to a wearer by positioning one of the waist regions, preferably the second waist region 29, under the wearer's back and drawing the remainder of the diaper 20 between the wearer's legs so that the other waist region, preferably the first waist region 27, is positioned across the front of the wearer. The tape tabs 36 of the fastening system are then released from the release portion. The diaperer then wraps the elasticized side panel around the wearer, while still grasping the tab portion. The fastening system is secured to the outer surface of the diaper 20 to effect two side closure.

The first topsheet 24 and the feces storage material 25 each have two major faces. The first topsheet 24 has a first major face oriented towards the wearer and an opposed second major face oriented towards the feces storage material 25. The feces storage material 25 has a first major face oriented towards the first topsheet 24, and an opposed second major face oriented towards the core 28, if it is separate from the feces storage material 25.

The first topsheet 24 is juxtaposed with, but not necessarily adjacent the body surface of the feces storage material 25, and is preferably joined to the backsheet 26 or feces storage material 25 by means such as those well known in the art. Suitable attachment means are described above with respect to joining the backsheet 26 to the absorbent core 28. In a preferred embodiment of the present invention, the first topsheet 24 and the backsheet 26 are joined directly to each other in the diaper periphery.

The first topsheet 24 is compliant, soft feeling, and non-irritating to the wearer's skin. Further, the first topsheet 24 is liquid pervious, permitting liquids (e.g., urine) to readily penetrate through its thickness. A suitable first topsheet 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. There are a number of manufacturing techniques which may be used to manufacture the first topsheet 24. For example, the first topsheet 24 may be a nonwoven web of fibers spunbonded, carded, wet-laid, meltblown, hydroentangled, combinations or composite laminates of the above, or the like. Further options for the first topsheets 24 include a carded/carded composite, hydroentangled over a wire forming screen and thermally air-through bonded by means well known to those skilled in the nonwovens art and hydroentanglement of fibrous webs. Particularly preferred are apertured formed films comprising a central layer of apertured films, being covered with non-woven material on both side, which also has apertures coinciding with the arrangement of apertures of the film.

U.S. Pat. No. 5,342,338 has pointed to the importance of the "Trans Topsheet capacity for low viscosity fecal material" (i.e. feces) as described therein. Thereby, the diaper 20 should have a trans-topsheet capacity of at least about 0.20 grams per square inch provided the diaper has at least 193 $cm^2$ (30 square inches) surface area. A particularly preferred execution related to an example whereby a combination of an apertured film/non-woven laminate (one example of which is PANTEX 18125X) as a topsheet together with an apertured film (one example of which is TREDEGAR X5790).

However, these trans-topsheet capacities are not sufficient to allow optimization of feces handling performance, in particular when also higher viscosity or higher consistency feces are considered. In these instances, not only the ease of penetrating through the element is relevant, but also the storage capacity of the storage material itself is relevant. Therefore, the trans-topsheet penetration test has been modified, such that now particularly useful materials could be screened out.

This "medium viscosity feces storage capacity test" is made (under standard laboratory conditions of 23 degree Celsius and 50% relative humidity) on a flat sample specimen of a size of 10 cm by 10 cm.

The material is covered by a perspex plate of same dimensions of 10 cm by 10 cm, and a thickness of 5 mm, having an hole of 3 cm diameter in the center of the plate, whereon a circular perspex tube of an inner diameter of also 3 cm is fixed. The height of this tube is 20 cm, and a cylinder is positioned inside such that it can smoothly glide inside the tube. (The tightness of the fitting is such that the test fluid as described below cannot be squeezed out under the applied pressure). A further part of the equipment is a weight to load the cylinder such that at its lower area a pressure of 5171 Pa (0.75 psi) is applied, and a further weight of 305 g to be placed on the perspex plate to submit the test specimen to a pressure of 427 Pa (0.0608 psi).

In order to be able to asses the material properties with regard to handling not only low viscosity materials, but also medium viscosity materials, the test fluid applied in this specific test is an aqueous solution of CARBOPOL ETD 2050, such as available from BF Goodrich Chemical (Deutschland) GmbH, Neuss, Germany. A particularly useful solution contains a 0.5% of this polymer, having—after careful preparation according to the standard procedure as provided by said supplier—, a viscosity of about 16000 cps also as according to the procedure given by said supplier for Brookfield viscometer.

For executing the test, the preweighed feces storage test specimen is cut to the desired size, and placed between (also preweighed) sheets of the same size of (i) a conventional polyethylene-film (such as used as backsheet material in diapers) and (ii) a standardized topsheet. For the higher viscosity materials an apertured film was particularly useful. Apertured film/nonwoven laminates are referred to and have been tested as supplied by Pantex S.A., Italy.

These are laminated composites, consisting of a layer of about 20 $\mu$m polyethylene film between two layers of a conventional spunbonded web of about 14 g/m2, made of polypropylene fibers. The webs are essentially as hydrophobic as polypropylene.

The apertures are essentially rectangular holes of about 0.5 $mm^2$ size punched by heated embossing pattern roll through all three layers. There are about 40 apertures per cm, covering approximately 20% of total surface. The bonding is achieved through the process of aperturing, where some melting of fibers occurs around the holes. This material is also disclosed in more detail in EP 0 207 904.

These sheets are carefully positioned and centered under the perspex plate. Then 20 g of test fluid is put into the tube, the cylinder is carefully fit into the tube, and the weights are applied both to perspex plate and the cylinder.

After 10 minutes testing time, the perspex plate as is carefully removed such that no further test fluid is transferred to or retained by the sheets beyond what has been picked up during these 10 minutes, and all three sheets are carefully weighted, whereby again care must be taken to separate these sheets without transferring test fluid from one layer to the other through that separation.

After weighing the test specimen, the area of the stain of test fluid in the specimen is determined by conventional methods, such as by measuring the diameter if sufficiently close to a circular distribution, or by using conventional Computerized Image Analysis tools, possibly including manually transfer of the stain size to a transparency.

The direct reading at the end of the test is the amount of material as picked up under the applied pressure during the testing time by the specimen and the stain size. In order to allow better comparison between materials and designs, the material basis capacity and the material capacity are calculated.

First, the material basis capacity is calculated (in g/cm$^2$) by dividing the amount of material picked up by the test specimen (in gram) by the size if the stain (cm$^2$). This parameter can then be used to design the size of the feces storage material.

The material capacity (in g/g) is the result of dividing the material basis capacity by the basis weight (in g/cm$^2$), thus giving the amount of fluid picked up per amount of material used. This parameter is important for designing material usages of the fecal storage materials.

Without wishing to be bound by the theory, is believed, that the mechanism of medium viscosity feces pick up is still dominated by capillary transport mechanisms, thus providing readily available storage space. Hence, the porosity and its dependency on applied pressures is important. However, a careful balance has to be met to not compromise too much on the softness of the materials. In order to compare the materials with regard to these properties, the materials were submitted to the resiliency test.

Thereby, samples were submitted in a conventional compression/pressure analysis equipment such as an INSTRON tester, which allows a constant crosshead speed of 10 mm per minute, and allow reading of crosshead position at certain pressure readings. Most conveniently, this can be achieved by plotting the compression curve and the graphically determining the calipers corresponding to a pressure of 1379 Pa, 2578 Pa, 3448 Pa, 5516 Pa and 6895 Pa (0.2, 0.4, 0.5, 0.8, and 1.0 psi), respectively. After reaching the highest compression, the pressure was reduced to 552 Pa (0.08 psi) for 5 seconds and the caliper was measured again. This cycle is repeated for three times, and the respective readings are averaged. The caliper readings then allow to calculate the respective thickness loss of the material at the given pressure, or after the cycle.

Useful materials to be applied in the present invention are open fibrous structures, and particularly useful materials are air laid, air through bonded nonwoven, using eccentric, polyethylene sheath/polypropylene core bicomponent fibers with a permanent incorporated into the polyethylene resin. Such webs provide open resilient fibrous structures, without compromising on the softness.

EXAMPLES

In order to exemplify the present invention, air laid, air through bonded nonwoven have been made by the applicant on a airlaying and air-through bonding line, using eccentric, polyethylene sheath/polypropylene core bicomponent fibers with a permanent incorporated into the polyethylene resin produced by DANAKLON Denmark, under the designation ESEWA, having a coarseness of 6.7 dTex. The web is disclosed in more detail in WO Patent 94/28838 assigned to Palumbo, the fibers used in EP 0 340 763 assigned to Hansen.

The comparative example is an apertured formed film, such as supplied by TREDEGAR under the designation X5790 as referred to in the above mentioned patent U.S. Pat. No. 5,342,338.

TABLE 1

|  |  | Test material | Comparative example |
|---|---|---|---|
| Basis weight | [gsm] | 60.0 | 62.2 |
| caliper (@ 552 Pa) | [mm] | 2.66 | 1.69 |
| density (@ 552 Pa) | [g/cm] | 0.023 | 0.037 |

TABLE 1-continued

|  |  | Test material | Comparative example |
|---|---|---|---|
| caliper loss |  |  |  |
| at max press. | [%] | 52.2 | 35.9 |
| after cycle | [%] | 19.4 | 18.4 |
| total test fluid pickup | [g] | 10.0 | 6.0 |
| stain size | [cm$^2$] | 44.4 | 54.7 |
| material capacity | [g/g] | 37.5 | 17.6 |
| material basis capacity | [g/cm$^2$] | 0.23 | 0.11 |

As can be clearly seen, the test materials provide significantly improved medium viscosity storage capacity, and also a much increased basis capacity.

Absorbent Article

Without wishing to be bound by the theory, it is believed, that when the feces is immobilized in the storage material, it does not return to soil or irritate the skin of the wearer. Furthermore, the low viscosity feces can be dewatered by the capillary action of the fluid handling components.

While a high capacity as such is preferred for optimized material usage, high basis capacities are preferred to allow more freedom when designing articles with improved fit (e.g. smaller articles), or improved urine handling capability which might be interfering with the feces storage.

Figure 3B:
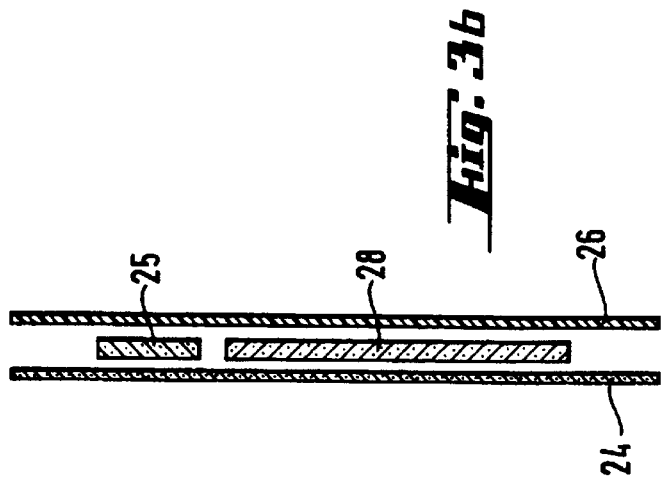
FIGS. 3a and b are a vertical sectional view taken along machine-directional lines 3—3 of FIGS. 1a and b, showing the relationship of the first topsheet, feces storage material and absorbent core.
Figure 3A:
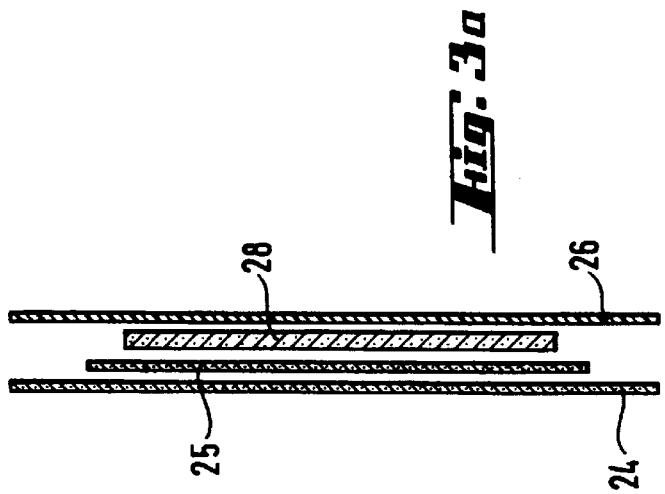
Figure 4:
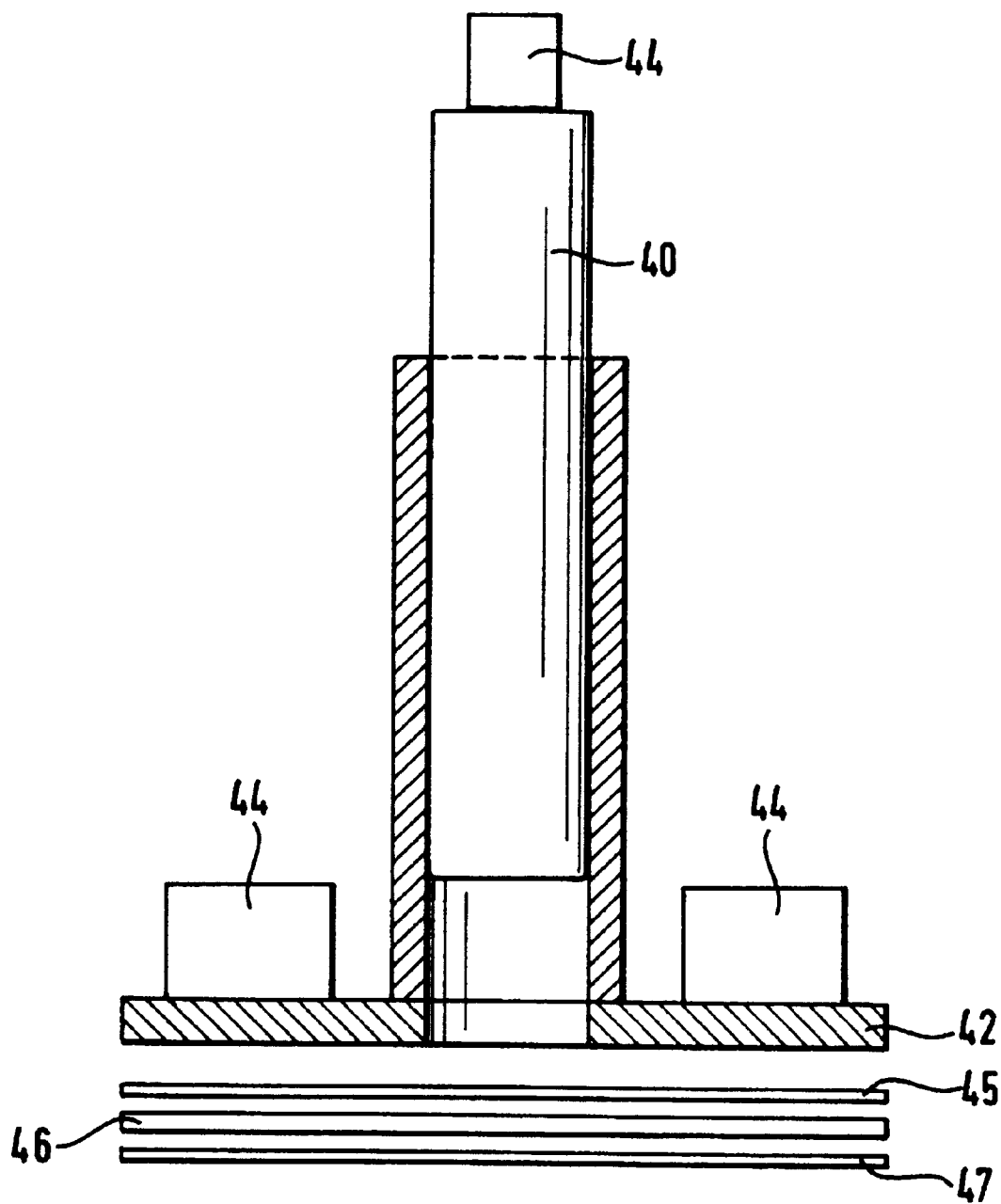
FIG. 4 is a schematic side view of an apparatus which may be used to measure the capacity of the disposable absorbent article.

Hence, absorbent articles comprising the feces storage materials according to the invention can be designed by simply inserting the feces storage material between the absorbent core 28 and the topsheet 24. Thereby, the amount (basis weight) and size of the feces storage material can be readily adjusted according to the needs of the intended wearer group. Thus, when for example designing an article for an amount of feces of 100 g, about 3 g of the above exemplified material are required, or about 500 cm$^2$, or a patch of about 33 cm length and 15 cm width would be required. Such a patch would cover essentially the total absorbent core for example in baby diapers of a conventional MAXI size. Such a design is indicated in FIGS. 1 to 3 in the respective parts "a".

An even preferred design is indicated in the "b" parts of the respective drawings, where by increasing the basis weight of the feces storage material the required size is significantly reduced. Then the feces storage materials can be advantageously be positioned in the rear part of the absorbent article, such that it is in registry with the anal opening, extending even further towards the back of the absorbent article.

In case the resulting thickness of the total structure exceeds acceptable values, the absorbent core 28 can be designed such that it is thinner or spared out in the region of the feces storage material.

In particular in such designs, it might further be advantageous to further exploit the capillary action and optimize it further. One specific aspect of the present invention is the to create channels in the feces storage material. Such channels can be achieved by conventional tools such as by removing material by cutting or scarfing. In this instance, the channels are defined by adjacent regions with respectively different material thicknesses or basis weights. Or, such channels can be created by densification (embossing) in certain areas of the fecal storage material. Then such channels are defined by adjacent regions of different densities. Alternatively, the channels can have both differences in thickness and basis weight and density altogether.

More preferably, such channels can be created by using a method described in more detail in European patent application 96108394.6, filed on May 28, 1996, describing a suitable material and a preferred execution for making such a material by a post formation treatment for a porous web by using two grooved rolls which are operated with such close tolerances, that the pores of the web are permanently deformed to a certain degree, thereby enhancing fluid transport properties.

With such structures it can be accomplished, that the discharged feces—or at least a part of these—can be distributed towards the rear part of the article.

What is claimed is:

1. A disposable hygienic article, comprising:

a liquid pervious first topsheet;

a liquid impervious backsheet at least partially peripherally joined to said first topsheet; and a feces storage material for pick up of low to medium viscosity feces intermediate said first topsheet and said backsheet;

characterized in that the feces storage material has a feces storage capacity of at least 20 g/g, when tested according to the described medium viscosity feces storage capacity test.

2. A disposable article according to claim 1, whereby said feces storage material having a feces storage capacity of at least 35 g/g.

3. A disposable article according to claim 1, whereby said feces storage material comprises a fibrous structure.

4. A disposable article according to claim 3, whereby said fibrous structure has not more than 55% caliper loss when submitted to the described resiliency test.

5. A disposable article according to claim 3, whereby said fibrous structure comprises channels in form of regions with different thicknesses or densities.

6. A disposable article according to claim 4, whereby the feces storage material is treated by the steps of feeding a web having fluid distribution properties between a pair of opposed pressure applicators comprising three-dimensional surfaces which are complementary to one another, and subjecting the portions of said web located between said opposed pressure applicators to incremental cross dimensional elongation by causing said opposed three-dimensional surfaces of said pressure applicators mesh with one another, whereby said web is at least partially permanently deformed.

7. A disposable absorbent article accoring to claim 1 wherein said first topsheet and said feces storage material are joined together essentially throughout their juxtaposed surface.

8. A disposable absorbent article according to claim 1, whereby the feces storage material is located only in the rear part of said absorbent article.

9. A disposable absorbent article according to claim 1, further comprising an absorbent core intermediate said feces storage material and said backsheet.

* * * * *